United States Patent [19]
> Bedner et al.

[11] Patent Number: 4,798,000
[45] Date of Patent: Jan. 17, 1989

[54] CUTTING BLADE ASSEMBLY

[76] Inventors: Richard J. Bedner, 113 Smoke Rise Dr., Warren, N.J. 07060; Emil Yerman, 2348 Terrace Ave., South Plainfield, N.J. 07080

[21] Appl. No.: 14,589
[22] Filed: Feb. 13, 1987
[51] Int. Cl.⁴ ............................................. B26B 1/10
[52] U.S. Cl. ..................................... 30/339; 128/305
[58] Field of Search ................ 30/329, 335, 337, 339; 128/305

[56] References Cited

U.S. PATENT DOCUMENTS

| | | | |
|---|---|---|---|
| 2,064,176 | 12/1936 | Parker | 30/337 |
| 2,708,313 | 5/1955 | Steele | 30/339 |
| 3,311,976 | 4/1967 | Matwijcow | 30/335 |
| 3,609,864 | 10/1971 | Bassett | 30/339 X |
| 4,173,071 | 11/1979 | Ishida | 30/339 |

Primary Examiner—Frank T. Yost
Assistant Examiner—Michael D. Folkerts
Attorney, Agent, or Firm—Robert A. Green

[57] ABSTRACT

A detachable cutting blade assembly includes an elongated handle having a rear end and a front end on which a cutting blade can be detachably supported and a blade-locking member, in the form of a wall, is secured to the top surface of the front end of the handle. A portion of the wall of the blade-locking member has lateral lips which give the wall a T-shaped cross section and this provides securement for a cutting blade. The lips of the blade-locking member are aligned with a hole in the handle and this permits the entire handle to be made with a two-part mold in a relatively inexpensive molding process.

11 Claims, 2 Drawing Sheets

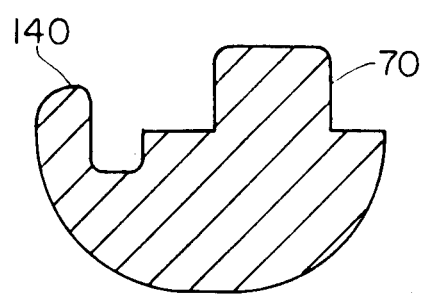
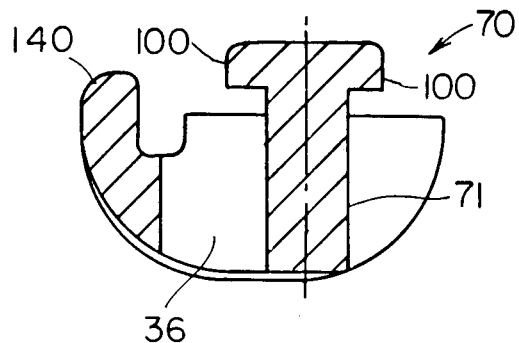
Fig. 4   Fig. 5
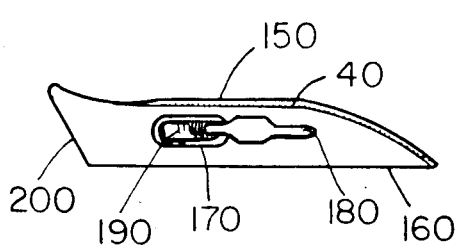
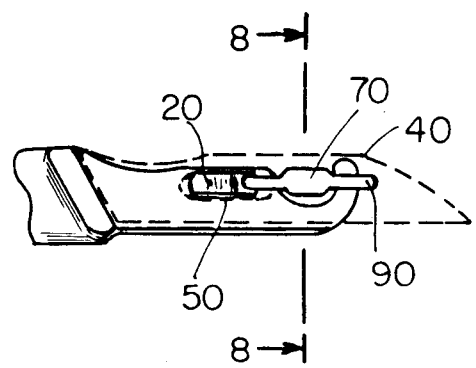
Fig. 6   Fig. 7
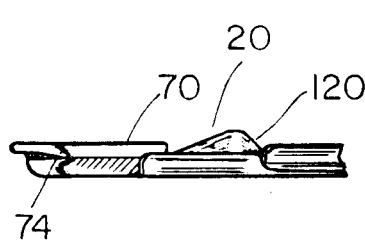
Fig. 9   Fig. 8

CUTTING BLADE ASSEMBLY

BACKGROUND OF THE INVENTION

At the present time, surgical scalpels comprise a handle to which cutting blades are attached. The handles may be of plastic but the preferred handle is made of metal because the weight and rigidity of metal assist the surgeon in operating. Because of this, the typical handle requires some machining to form parts to which a blade can be secured and as a result, the handle is relatively expensive and is not considered a disposable device.

The present invention provides a handle for a detachable surgical blade, the handle being of metal but being so constructed that it lends itself to lower-cost manufacturing methods than prior art metal handles. Although the handle is inexpensive enough to be disposable, it is so constructed that it can be re-used for a relatively large number of times. In addition, the handle of the invention provides improved support for surgical blades of different sizes.

DESCRIPTION OF THE DRAWINGS

FIG. 4 is a sectional view along the lines 4—4 in FIG. 1;

FIG. 5 is a sectional view along the lines 5—5 in FIG. 1;

FIG. 6 is a plan view of a cutting blade usable with the handle of invention;

FIG. 7 is a plan view of the front end of the handle of FIG. 1 showing a blade coupled thereto;

FIG. 8 is a sectional view along the lines 8—8 in FIG. 7;

FIG. 9 is a side elevational view of a portion of the handle of FIG. 1; and

DESCRIPTION OF THE INVENTION

Figures 1, 2, 3, 10:
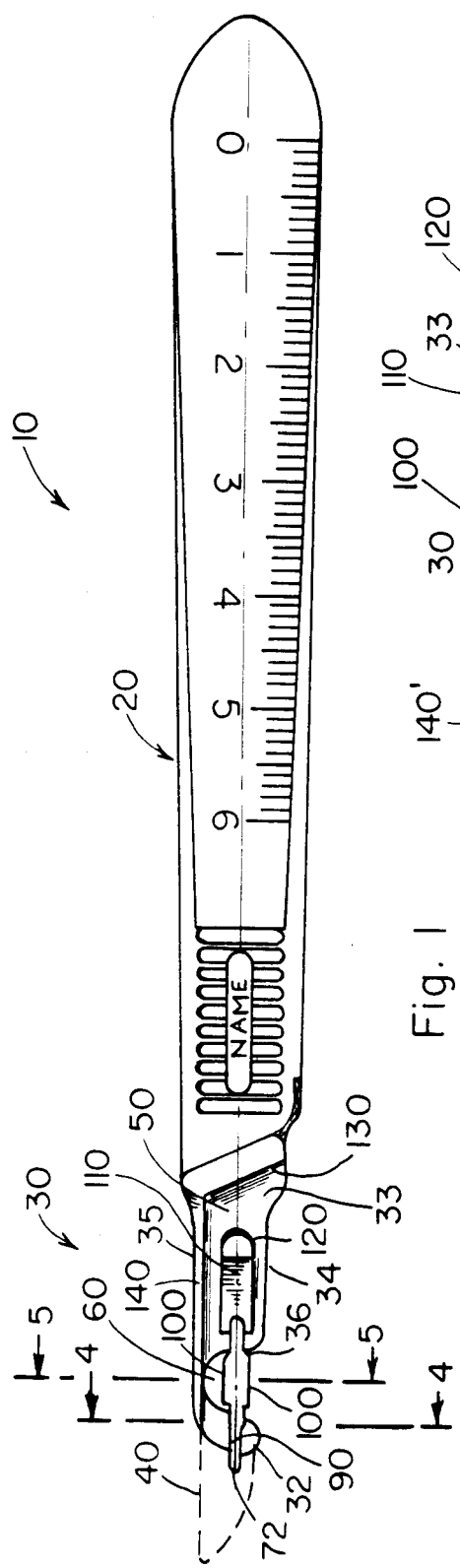
FIG. 1 is a plan view of a scalpel handle embodying the invention.
FIG. 2 is a perspective view of the blade support, front end, of the scalpel handle of FIG. 1.
FIG. 3 is a side elevational view of the handle of FIG. 1.
FIG. 10 is an enlarged view of a portion of the handle of the invention showing a modification of a portion thereof.

The principles of the invention are described and illustrate with respect to a surgical scalpel and the handle thereof but it will be clear to those studying the invention that these principles may be employed in other areas.

A detachable cutting blade assembly 10, referring to FIG. 1, includes a handle 20 having a front end 30 to which a cutting blade 40 can be detachably secured. The front end 30 of the handle has a smaller thickness than the rest of the handle and it includes a leading tip end 32, a rear end 33, a lower edge 34 and an upper edge 35. A generally U-shaped opening or hole or slot 36 is provided in the front end of the handle, toward the leading tip end thereof and extending inwardly from the lower edge 34 to near the upper edge 35. The front end 30 of the handle has a generally flat top surface 50 and bottom surface 51 and a blade-locking member 70 extends along the top surface 50, lying along the long axis of the handle. The blade-locking member comprises a generally vertical wall (FIGS. 3 and 4) which rises from the top surface 50 and extends along a portion of the top surface 50 from the leading tip end 32 to near the center thereof. The blade-locking member 70 includes lips 100 (FIGS. 1, 2 and 5) which extend laterally from the upper and lower edges (as seen in FIG. 1) of the top surface of the locking member wall to give the locking member a T-shaped cross section (FIG. 5) which can engage and couple to and hold a surgical blade, with lips 100 holding the blade. The lips 100 lie within the area of the hole 36 as can be seen in FIG. 5 which is a view looking upwardly from the bottom of the front end (FIG. 4) of the handle through the hole 36 which extends through the body of the front end of the handle from the top surface 50 to the bottom surface 51. In addition, the locking member includes a wall portion 71 which extends down into and across the hole 36 as seen in FIGS. 3 and 5. The utility of this arrangement is discussed below and relates to the manufacture of an inexpensive handle.

The tip 72 of the locking member 70 may extend slightly beyond the leading tip end of the front end 30 itself.

Rearwardly of the locking member 70, the top surface 50 of the front end 30 carries a ramp 110 which rises from the top surface as it proceeds rearwardly aligned with the locking member and the long axis of the handle. At its rear end, the ramp 110 terminates in a wall which is also in the form of a ramp 120 which slopes downwardly toward the rear end 33 of the front end of the handle. The rear end of the front end of the handle terminates at a slanted surface or wall 130 (slanted at an angle to the longitudinal axis of the handle) against which a surgical blade 40 rests when it is coupled to the handle.

The front end of the handle also includes a wall 140 which extends along the upper edge 35 and rises above the top surface 50. The wall 140 provides a shoulder against which a surgical blade bears when secured to the handle.

The front end of the handle and the above described locking member 70 and ramp 110 carried thereby are shaped to provide locking engagement with standard surgical blades 40 which, at the present time, are all generally of the same construction. All such blades (FIG. 6) have a slot which permits them to be coupled to a handle. A typical surgical blade 40 includes a lower cutting edge 150 and an opposite upper edge 160 and a longitudinal slot 170 used in coupling the blade to the handle 20. The slot 170 includes a narrow front portion 180 which receives the locking member 70 and slips under the lips 100 and is held in place thereby. The rear portion 190 of the slot 170 is wider to receive the ramp 110 and is about the same width as the ramp 110.

Referring to FIGS. 7 and 8 in coupling the blade 40 to the handle 20, the blade is seated on the front end 30 with the locking member 70 in the wide rear portion 190 of the slot 170 and it is pushed rearwardly. The rear portion of the blade slides up the ramp 110 thereby facilitating the operation and the narrow portion 180 of the slot 170 slips under lips 100 and engages the locking member 70. When the blade is in place, the rear edge of the slot 170 slides down the end ramp 120 to a final position determined by the total length of the slot 170.

It can be seen that the end ramp 120 provides tolerance for variations in the length of the slot 170 from blade to blade. If the slot is slightly short, the rear end of the slot stops in contact with an upper portion of the rear or end ramp and if the slot is somewhat larger, the rear end of the slot moves farther down the end ramp but always in contact therewith.

The rear end or edge 200 of the blade 40 is slanted to bear against and match the slant of the slanted wall 130 of the handle and the upper edge 160 of the blade bears against the upper wall or vertical tip 140 of the front end of the handle. The tip 72 and leading end 90 of the locking member 70 provide a stiffening support against which the blade 40 bears in use.

In a modification of the invention illustrated by dash lines in FIG. 1, the upper wall 140 of the front end of the handle is extended forwardly a suitable distance to provide an extended wall 140'. The wall 140' provides support for especially large or long surgical blades. Wall 140' may extend an additional ½" or 1" or more or less as required.

Under some circumstances, if the handle 20 is used as a disposable, the top of ramp 120 may be deformed by pressure to overlay the portions of the slot 190 in the blade 40 and thus provide additional locking means for holding the blade in place.

Normally, if it were desired to mold a handle 20 having a front end 30 of the type described above, including the locking member 70 having lips 100 and a T-shaped cross section, a multi-part mold would be required, including a removable rod to form the T-shaped portion of the locking member. This is a relatively complex and expensive molding operation. However, the provision of the hole 36 aligned with the lips 100 permits a relatively inexpensive two-part mold to be used. One part of the mold includes two posts which form the hole 36 and cooperate with the second part of the mold to form the lips 100 on the locking member.

In a modification of the invention, the front end of the "T" structure of the blade locking member 70 formed by the lips 100 is tapered and provided with a sloped front wall 74 having a negative slope as seen in FIG. 10. The wall 74 thus slopes downwardly and rearwardly and this slope allows a blade to align itself as it is coupled to the handle 20.

What is claimed is:

1. A cutting blade support assembly including
   an elongated blade support member adapted to be carried in the hand, said blade support member having a rear end and a front end on which a cutting blade can be detachably supported,
   said front end having a top surface on which a cutting blade can be seated, and
   a blade locking member in the form of a wall extending along the front end of said blade support member generally parallel to the longitudinal axis thereof,
   a portion of said wall of said blade locking member having a T-shaped cross section which is adapted to be engaged by a blade to hold the blade in place,
   the T-shape including a vertical wall having an upper end from which a top horizontal surface extends and provides lips on either side of said vertical wall, said lips being adapted to be engaged by a blade, and
   a slot in said front end of said blade support member and extending therethrough from said top surface thereof to the bottom surface thereof in alignment with said horizontal lips, said vertical wall extending longitudinally across said slot and said lips vertically overlying and lying across said slot,
   whereby said T-shaped locking member may be formed by a two-part mold including cooperating members forming said slot, said vertical wall and said locking member lips.

2. The apparatus defined in claim 1 wherein said lips extend laterally from the top surface of said wall.

3. The apparatus defined in claim 1 and including on the top surface of said front end, a ramp aligned with said blade locking member and positioned rearwardly thereof, said ramp rising as it proceeds rearwardly, said ramp facilitating the coupling of a blade to the front end of said elongated member whereby the blade slides up the ramp and engages the rear end thereof as it is coupled to the front end of the elongated member.

4. The apparatus defined in claim 1 wherein said front end of said blade support member includes an upper edge and a lower edge, and a support wall rises from the upper edge of said front end of said blade support member, said support wall providing a surface against which a blade bears when the apparatus is used to perform a cutting operation.

5. The apparatus defined in claim 4 wherein said support wall is substantially the same length as said front end of said blade support member.

6. The apparatus defined in claim 4 wherein said support wall is considerably longer than the front end of said blade support member to provide extra support for a long cutting blade.

7. The apparatus defined in claim 1 wherein the leading edges of said lips are shaped to provide walls which taper downwardly and rearwardly to facilitate the coupling and alignment of a blade thereto.

8. The apparatus defined in claim 1 wherein said top surface of said front end of said blade support member includes a blade support including a first surface portion having a positive slope and a second portion having a negative slope.

9. The apparatus defined in claim 1 wherein said slot has a semicircular cross section.

10. A cutting blade support assembly including an elongated blade support member adapted to be carried in the hand, said blade support member having a rear end and a front end on which a cutting blade can be detachably supported,
    said front end having a top surface on which a cutting blade can be seated,
    a blade locking member in the form of a wall extending along the front end of said blade support member generally parallel to the longitudinal axis thereof,
    a portion of said wall of said blade locking member having a T-shaped cross section which is adapted to be engaged by a blade to hold the blade in place;
    on the top surface of said front end, a ramp aligned with said blade locking member and positioned rearwardly thereof, said ramp rising as it proceeds rearwardly, said ramp facilitating the coupling of a blade to the front end of said elongated member whereby the blade slides up the ramp and engages the rear end thereof as it is coupled to the front end of the elongated member, and
    a second ramp at the rear end of said ramp and having a slope opposite to the slope of said ramp.

11. A cutting blade support assembly including an elongated blade support member adapted to be carried in the hand, said blade support member having a rear end and a front end on which a cutting blade can be detachably supported,
    said front end having a top surface on which a cutting blade can be seated, said front end having a leading portion in the shape of a U-shaped, hook-like member defining a hole in said front end, and a blade locking member secured to said top surface of said front end and extending across the hole defined by said U-shaped, hook-like member, said blade locking member including a portion having a T-shaped cross section made up of a vertical wall and horizontal lips extending laterally from the top of said vertical wall, said T-shaped cross section permitting the engagement of a blade therewith to hold the blade in place beneath said lips, said lips of said blade locking member overlying said hole in said U-shaped, hook-like member whereby said T-shaped cross section of said blade locking member can be formed by a two-part mold including a first part inserted through said opening from beneath said front end of said blade support member and a second part between which the T-shape is formed.

* * * * *